United States Patent [19]

Modabber

[11] 3,988,115

[45] Oct. 26, 1976

[54] DIAGNOSTIC METHOD FOR DETERMINING PATHOLOGICAL CONDITION BY ANTIGEN-COMBINING CAPACITY OF LYMPHOCYTES

[76] Inventor: Farrokh Z. Modabber, P.O. Box 1310, School of Public Health, Teheran University, Teheran, Iran

[22] Filed: Sept. 18, 1975

[21] Appl. No.: 614,360

[52] U.S. Cl. .................... 23/230 B; 195/103.5 R; 424/12; 424/88; 424/89; 424/91; 424/92
[51] Int. Cl.² .................................... G01N 33/16
[58] Field of Search ............ 23/230 B; 195/103.5 R; 424/12

[56] References Cited
UNITED STATES PATENTS

| | | | |
|---|---|---|---|
| 3,654,090 | 4/1972 | Schuurs | 424/12 |
| 3,816,263 | 6/1974 | Rabin | 195/103.5 R |
| 3,843,324 | 10/1974 | Edelman | 424/12 X |
| 3,900,558 | 8/1975 | Kinsolving | 424/12 X |

OTHER PUBLICATIONS

Chemical Abstracts, 75: 149952t (1971).
Chemical Abstracts, 78: 146065g (1973).
Chemical Abstracts, 80: 80983n (1974).

*Primary Examiner*—Morris O. Wolk
*Assistant Examiner*—Sidney Marantz

[57] ABSTRACT

A method for determining in a patient the presence or absence of a pathological condition producing a specific immune response. The antigen associated with the pathological condition is labeled and added to a sample of the patient's lymphocytes and to a control sample. Comparison of the antigen-binding capacity of the patient's lymphocytes to that of the control sample is related to the presence or absence of the pathological condition.

14 Claims, No Drawings

DIAGNOSTIC METHOD FOR DETERMINING PATHOLOGICAL CONDITION BY ANTIGEN-COMBINING CAPACITY OF LYMPHOCYTES

BACKGROUND OF THE INVENTION

This invention relates to the detection, in a patient, of a pathological condition known to produce an immune response.

It is known that a number of pathological conditions, or diseases, cause the production of an immune response in the body. A variety of pathological conditions, for example, produce antibodies in the serum which are specific to a particular pathological condition and bind to antigens associated with that condition to help to protect the body from the onslaught of the pathological condition, and in some cases, to provide immunity against possible future onslaughts.

It is also known that the presence or absence of a particular pathological condition in a patient can frequently be detected by testing the patient's serum for the presence of antibodies, or of an abnormal number of antibodies, to an antigen associated with the pathological condition, the antibodies being detectable by the attachment thereto of the counterpart antigens.

While detection and diagnostic methods based on the presence of antibodies in serum are quite useful, their usefulness is limited by the time that is required before antibodies are formed in the serum in sufficient quantity for effective detection so that the methods cannot be used for diagnosis in the early stages of the disease, which early stages are frequently critical for effective treatment.

In addition, there are certain pathological conditions which produce an immune response but do not produce large amounts of antibodies readily detectable in the serum. Such conditions cannot be diagnosed or detected by serological testing.

SUMMARY OF THE INVENTION

In accordance with the present inventon a specific pathological condition is detected by the presence in the blood of an abnormal number of lymphocytes having receptors which can bind to an antigen associated with the specific pathological condition. Specifically, the invention provides a method for determining in a patient the presence or absence of a pathological condition which produces at least one specific immune response which comprises:

a. extracting from the patient a sample of blood, b. providing a control sample containing particles of predetermined binding activity with respect to an antigen associated with said pathological condition, generally a sample of blood from at least one individual free of said pathological condition, c. adding to at least the lymphocyte fraction of said patient's blood and of said control blood an excess of a detection agent comprising an antigen for said pathological condition linked to a marker material whereby a portion of said detection agent attaches to a portion of the lymphocytes in said lymphocyte fraction, d. eliminating from each of said lymphocyte fractions any unattached detection agent, e. determining the amount of attached detection agent in each of said lymphocyte fractions through determination of the amount of said marker material therein and calculating the amount of attached detection agent in each of said lymphocyte fractions per designated number of white blood cells, and f. comparing the amount of said marker material per designated number of white blood cells in said blood of said patient with the amount of said marker material per designated number of white blood cells in the blood of said control sample.

It is known that the lymphocytes in the bloodstream are of two principal types which have been designated as "B" cells and "T" cells. The "B" cells originate in bone marrow. The "T" cells may also be originated in bone marrow but are modified in some way by the thymus gland. Both types of lymphocytes participate in protecting the body against the effects of antigens in the bloodstream by binding the antigens to specific antigen receptors on the lymphocyte surfaces.

Lymphocytes which appear morphologically identical when viewed under a microscope actually differ in the nature of the antigen receptors on their surfaces. There are thousands of types of lymphocytes based on specific antigen receptors on their surfaces with a few of each type in each million lymphocytes.

With the incursion of an antigen into the host, the antigen interacts with the lymphocytes which have receptors specific to the antigen; and this stimulates such lymphocytes to repeated reproduction, or mitosis, resulting in the substantial proliferation of the number of such lymphocytes.

Some antigens stimulate the proliferaion of "T" cells, only; some stimulate "B" cells, only; but most antigens stimulate the proliferation of both "T" cells and "B" cells having specific antigen receptors on their surfaces.

The "B" cells, after a certain amount of proliferation, are converted to plasma cells which produce antibodies to the specific antigen; and the antibodies pass into the serum, gradually building up in concentration therein. Serological diagnostic techniques are dependent on the detection and measurement of these antibodies. They cannot be relied on to detect a pathological condition before a substantial amount antibody is produced. They are therefore, ineffective as diagnostic tools in the early stages of any abnormal pathological condition, ineffective to detect some conditions which do not generate "B" cell proliferation, and ineffective to detect some conditions which produce antibodies in numbers too small to be identifiable in the serum.

Ainti et al., in an article entitled "Surface Markers on Lymphocytes of Patients with Infectious Diseases", Infection and Immunity, vol. 8, no. 1, July 1973, pp. 110–117, describe an attempt to correlate the presence or absence of certain infectious diseases with the relative amounts of lymphocytes having three specific types of surface markers: (i) surface immunoglobulines, (ii) receptor for C3 complement component (EAC test), and (iii) spontaneous binding of sheep red blood cells (rosette formation). No distinct correlations were noted.

The instant invention is predicated on the detection of an abnormally large binding capacity in the lymphocytes of a patient (whether "B" cells or "T" cells) for a specific antigen of a pathological condition in order to determine whether the patient has the disease or pathological condition associated with that antigen, or in some cases to determine whether the patient has built up an immunity to the disease by a prior proliferation of such lymphocytes. Since the lymphocytes detected by the procedure of this invention proliferate prior to the production of antibodies, the procedure is capable of detecting a pathological condition sooner than any serological method.

The specific steps of the procedure of the instant invention are as follows:

a. a sample of blood is drawn from a patient into a receptacle containing an anti-clotting agent, such as heparin;

b. the cellular material is separated from the plasma fraction (this step may be omitted, if desired;

c. a measured amount of a disease-associated antigen coupled to a detection agent, such as an enzyme, is added to a measured amount of blood cells or whole blood, and the mixture is allowed to stand for a period of time (such as 30 minutes) to enable the antigen portion of the couple to link itsellf to lymphocytes containing receptors to the particular antigen;

d. the blood cells in the mixture are repeatedly washed and all of the antigen-detection agent complex which is not attached to lymphocyte receptors is washed away (alternatively, the unbound antigen-detection agent complex is inactivated);

e. a cell count is made to determine the total number of white blood cells in a given amount of the sample;

f. the washed blood cells are assayed by means of the remaining detection agent complex therein to determine the amount of the antigen-detection agent complex bound; and f. the amount of antigen-detection agent bound to a given number of lymphocyte receptors for the particular antigen is calculated from the white blood cell count of step (e) and the enzyme activity of step (b) and compared to the amount of antigen-detection agent complex bound to a given number of lymphocytes in the blood of the normal persons who do not have the pathological condition being tested for or compared to a prepared control sample containing particles of predetermined binding activity with respect to an antigen associated with said pathological condition.

A preferred detection agent for coupling to an antigen is an enzyme which can be detected by its enzymatic action because the sensitivity of any test for enzymatic action can be adjusted by the time permitted for the action to proceed before the measurement thereof. Beta-galactosidase, for example, is known as capable of acting on a colorless, fluorogenic substrate to yield fluorescein which is quantitatively detectable by the intensity of its fluorescence. In a test where lymphocytes containing a particular antigen receptor are expected to be present in relatively small amounts, the sensitivity of the test for beta-galactosidase linked thereto (through the antigen) may be enhanced by providing an extended time for the enzyme to act on the fluorogenic substrate.

Among the pathological conditions that may be diagnosed by the technique of this invention are infectious diseases caused by bacteria, viruses, Rickettsiae, protozoa, fungi and helminths or any agent producing an immune response such as chemicals or drugs capable of producing an allergic response. Examples of such diseases include gonorrhea (caused by *Neisseria gonorrheae*), amebiasis (caused by *Entamoeba histolytica*) and histoplasmosis (caused by *Histoplasma capsulatum*).

Other conditions producing immune responses may also be diagnosed by the technique of this invention, including tumorassociated conditions such as sarcomas, carcinomas (e.g. of the colon or breast) and lymphomas. The invention is also useful in that it enables the detection of specific allergic sensitivities by an in vitro test.

The antigens for specific pathological conditions which are useful for diagnosis of these conditions in accordance with this invention include antigens commercially available for use in other diagnostic tests and disclosed in the technical literature. For the diagnosis of amebiasis, or example, a suitable stabilized antigen is prepared from defined cultures of *Entamoeba histolytica* in accordance with procedures described in an article by Paul E. Thompson, Susanne K. Gradel, Curt R. Schneider, William P. Stucki and Ruth M. Gordon, entitled "Preparation and Evaluation of Stabilized *Entamoeba histolytica* from Axenic Cultures of *Entamoeba histolytica*", 1968. Bull. Org. Health 39:349–365.

This stabilized antigen for diagnosis of amebiasis is commercially available as *Entamoeba histolytica* HK9 and is used in a slide agglutination test for amebiasis.

The antigen in the technique of the present invention is coupled to the detection agent through a coupling agent which is a bifunctional compound capable of reacting with and linking with carboxyl or amino groups on the antigen and on the enzyme, or other detection agent. Glutaraldehyde is a suitable coupling, or conjugation agent. Other suitale coupling agents include water soluble carbodiimides (ECDI), pyruvaldehyde, activated diazonium compounds such as bis-diazotized benzidine (BDB) and the alkyl chloroformates.

In addition to the beta-galactosidase disclosed above, other enzymes such as lysozyme may be used as the detection agent. Alternatively the detection agent may be a radioactive material containing a radioactive atom such as $^3H$, $^{14}C$, $^{131}I$ or $^{125}I$. In still other embodiments the detection agent conjugated to the antigen may be a material detectable by highly sensitive equipment and techniques such as nuclear magnetic resonance spectrometry or electron spin (paramegnetic) spectroscopy.

PREPARATION OF REAGENTS AND PROCEDURES a. Preparation of the bis-diazotized benzidine coupling agent (BDB) [following the method disclosed in Methods in Immunology and Immunochemistry by Williams and Chase, vol. I, p. 165]

0.23 g of benzidine was dissolved in 45 ml of 0.2N HCl. To this solution which was kept at 0° C. with constant mixing, 0.175 g of $NaNO_2$ dissolved in 5 ml of distilled water was added dropwise. The reaction was allowed to proceed for 30 minutes. The mixture was standardized according to the technique described below, distributed in 2 ml vials, frozen in a dry ice-acetone bath and kept at −70° C. until used.

b. Standardization of bis-diazotized benzidine (BDB)

To test the potency of each BDB preparation, 0.5 ml of BDB was mixed with 7 ml of phosphate buffer, pH 7.2, with 0.001 M $MgSO_4$, 0.002 M $MnSO_4$ ($PM^2$) at time 0. The characteristic reaction was a color change from lemon yellow to a deep reddish brown and the development of turbidity within 90 seconds. Whenever more than 95 seconds was required for development of turbidity, a crystal of benzidine was added to the stock solution and the test was repeated. Whenever turbidity developed in less than 85 seconds, 1–2 drops of 10% $NaNO_2$ was added to the stock solution.

The bis-diazotized benzidine, prepared as above was used to couple amebic antigen (prepared as described below) with a commercially available purified betagalactosidase of E-coli ML 308 having a molecular weight of $5.4 \times 10^5$ Daltons.

c. Amebic antigen

Stabilized antigens from *Entamoeba histolytica* were prepared by the method described in "Preparation and Evaluation of Stabilized *Entamoeba Histolytica* from Axenic Cultures of *Entamoeba Histolytica*" by Paul E. Thompson et al. Bull. Org. Health 39:349-365 (1968), which publication is incorporated herein by reference.

An axenic strain of *Entamoeba histolytica* HK 9 was grown in a liquid medium comprising a monophasic liquid medium containing liver digest, tryptic digest of casein, glucose, reducing agents (cysteine and ascorbic acid), buffers, sterile horse serum and a mixture of vitamins for three days at 37° C. and the ameba was isolated by centrifugation.

Prior to centrifugation the flask containing the ameba was chilled quickly by immersion for ten minutes in iced water to dislodge ameba adhering to the glass surface. The ameba were then concentrated at $550 \times g$ for 15 minutes and washed three times in 50 ml of 0.25M sucrose and finally resuspended in pH 7.2 phosphate buffered saline to approximately $10 \times 10^6$ ameba per ml.

The amebic suspension was ultrasonicated for 1 to 2 minutes in an ice water bath and this preparation was centrifuged at $550 \times g$ for 15 minutes to remove the few remaining large particles. The resulting opalescent supernatant liquid was lyophilized.

The nitrogen content of the lyophilized material was determined by standard Kjeldahl analysis and the lyophilized material was diluted to a nitrogen content of 1.8 mg per ml.

d. Preparation of the substrates

One of the substrates used was orthonitrophenyl beta-D-galactopyranoside (ONPG) which was used for all determinations of enzymatic activity of free enzyme and of antigen-enzyme (A-Z) conjugate. This substrate was diluted to a final concentration of M/75 in 0.25 M $PM^2$ and was kept frozen (at $-20°$ C.) in aliquots of 10 ml each. Samples were thawed prior to use. The other substrate used was fluorescein-di-beta-galactopyranoside. This compound is not fluorescent as such. It is composed of two fluorescein molecules conjugated to the galactose molecule by beta glycosidic bonds at the hydroxyl sites. Upon the hydrolysis of one or both of these glycosidic bonds, fluorescein monogalactoside or free fluorescein is produced, respectively, both of these products are fluorescent with similar absorption-emission spectra.

e. Reducing agents

The enzyme is enhanced in activity and stability in the presence of a reducing agent. For this reason, a reducing agent (0.1 molar 2-mercaptoethanol) was used in the buffer ($PM^2$) in the manner described above.

Alternatively, the reducing agent used was dithiothriotol (DTT) at a final concentration of 0.001 M.

f. Enzyme assay

The orthonitrophenyl beta-D galactopyranoside (ONPG) was assayed by liberating orthonitrophenyl therefrom and comparing the optical density (OD) of the residue with the optical density of a control containing $PM^2$ buffer in place of the enzyme.

One ml of dilute enzyme was mixed with 1 ml of $PM^2$ (defined above) containing 0.1 M 2-mercaptoethanol. The mixture was allowed to stand in a water bath at 29° C. for 10 minutes. 0.6 ml of ONPG solution equilibrated at 29° C. was added to the mixture and the time was recorded ($t = O$). The mixture was incubated at 29° C. for about 2 to 5 minutes or until a yellow color was produced by the liberation of orthonitrophenyl. To stop the reaction 1.4 ml of 1 M $Na_2CO_3$ was added at time marked as $t_1$. Samples were removed from the water bath and the optical density was determined using a spectrophotometer against a "ONPG control" in which 1 ml of $PM^2$ replaced the enzyme in the above mixture.

g. Calculation of units of enzyme

By definition one unit of enzyme is the amount of enzyme which can produce 1 nanomole of ONP in 1 minute at 29° C. It is calculated from the following equation:

Units of enzyme $$(UZ) = \frac{\text{O.D. of sample} \times \text{volume of mixture}}{\text{O.D. of 1 nanomole of ONP at 420 nm} \times \text{time}}$$

The OD of 1 nanomole of ONP at 420 nm is 0.005. If the OD of the test sample equals A, and the volume of the reaction equals 4, the following equation is derived:

$$UZ = \frac{A \times 4}{0.005 \times \text{time}} = \frac{A \times 800}{\text{time}}$$

The amount of enzyme per ml was calculated from the following equation:

$$\text{mg } Z = \frac{UZ}{4 \times 10^5}$$

in which $4 \times 10^5$ is the specific activity of Z under the conditions of testing. The specific activity is defined as the enzymatic activity of 1 mg of pure enzyme.

h. FDBG assay

This assay was used only to measure cell bound enzymatic activity.

0.2 ml of processed cell suspension (see I-Z assay, herebelow) was mixed with 0.2 ml of $2.4 \times 10^{-5}$M FDBG. The mixture was incubated at 29° C. and at various intervals the amount of fluorescent product was measured using a Turner fluorometer. The rate of increase in fluorometer units was directly proportional to the amount of A-Z (amebic antigen-enzyme conjugate) which was bound to the cells. The activity of $10^6$ cells was calculated by the following formula and was compared for different cell suspensions, converting the measurements of fluorometer units per $10^6$ cells per hours:

$$\frac{\text{increase in fluorometer reading} \times 10^6 \times 60}{\text{No. of cells tested} \times \text{minutes}}$$

i. Conjugation of amebic antigen to Z(A-Z)

One ml of enzyme solution containing 3 mg of enzyme was dialyzed overnight against one liter of phosphate buffer solution ($PM^2$) containing 0.1 M of 2-mercaptoethanol (ME) and having a pH of 7.2 0.5 ml of the dialyzed enzyme was placed in a small flat bottom tube with 0.5 ml of reconstituted amebic antigen (1 mg) and the mixture was stirred constantly at 0° C. Meanwhile a frozen BDB sample was thawed and diluted 1:15 in $PM^2$. 0.2 ml of the diluted BDB was added to the enzyme-amebic mixture as quickly as possible. The reaction mixture was maintained at 0° C. for 15 minutes and then dialyzed against $PM^2$ overnight. The solution was designated A-Z conjugate and found to be enzymatically active. One drop of merthiolate (1:1000) was added to prevent microbial growth.

j. Preparation of cell suspension (alternatively,

The buffy coat was obtained from heparinized blood (of test patients or of human or animal controls) by centrifuging at 750 × g for 20 minutes. Plasma was removed and the buffy coat containing the lymphocytes was fixed by the addition of 10 ml of 4% formaldehyde in $PM^2$ per ml of blood cells (alternaively, 2% of glutaraldehyde could be used). The fixed cells were stored at 4° C. until tested.

k. Immunoenzymatic assay (I-Z)

Fixed blood cells were washed twice with about 10 times their volume of $PM^2$ to remove formaldehyde with centrifuging after each wash at 750 × g for 5 minutes. White blood cells stained with Turk's solution (0.01% crystal violet in 2% acetic acid) and were enumerated using a hemocytometer 100 micrograms of A—Z was added to each ml of cell suspension containing approximately $10^7$ cells. The mixture was incubated at 37° C. for one hour to allow time for the specific antigen binding cells which bear amebic receptors to bind A—Z conjugate.

To remove the unbound A-Z, samples were washed 4 times with 35 ml of $PM^2$ containing ME and centrifuged after each wash at 750 × g for 5 minutes at 4° C. The washed cells were resuspended in 2 ml of $PM^2$ and the white blood cells were counted again. Samples were diluted so that all contained approximately the same number of lymphocytes. The enzyme bound to the cells was assayed using 0.2 ml of cell suspension and 0.2 ml of $4.8 \times 10^{-5}$ molar FDBG. The rate of production of fluorescence was measured by a Turner fluorometer at various intervals. The results were recorded as increase of fluorometer units in one hour produced by $10^6$ lymphocytes.

TEST RESULTS

In each of the following series of tests (run in Shiraz, Iran where amebiasis is endemic), blood samples from a group of patients were subjected to testing by the above described procedure to determine the I—Z units and compared with a sample of normal blood as a control. In each group of patients there were one or more who had been clinically diagnosed as having hepatic amebiasis on the basis of liver scan and response to anti-amebic drugs and/or one or more who had been diagnosed clinically as having some other abnormal pathological condition, including some who had non-amebic lesions in their liver scans. The sera of all patients were also tested for amebiasis by the commercially available latex agglutination test and the response of the patients to anti-amebic drugs, when administered, was also recorded.

GROUP I

| Patient Code No. | Latex Agglutination | I-Z Units | Clinical Diagnosis | Sex | Age | Response to anti-amebic drugs |
|---|---|---|---|---|---|---|
| 1 | − | <1 | Cirrhosis & diabetes | F | 50 | N.T.* |
| 2 | + | 19 | Amebic hepatitis | F | 20 | + |
| 3 | + | 17 | Amebic liver abscess | M | 45 | + |
| Normal | − | <1 | — | — | — | N.T. |

*N.T. = No treatment

GROUP II

| Patient Code No. | Latex Agglutination | I-Z Units | Clincial Diagnosis | Sex | Age | Response to anti-amebic drugs |
|---|---|---|---|---|---|---|
| 4 | − | <1 | Thalessemia | F | 27 | N.T.* |
| 5 | + | 19 | Amebic liver abscess | M | 47 | + |
| 6 | − | <1 | Hyperspleenism of unkown etiology | F | 23 | N.T. |
| 7 | + | <1 | 1) Duodenal ulcer 2) Intra-abdominal abscess due to old duodenal ulcer perforation | M | 40 | N.T. |
| Normal | − | <1 | — | — | — | N.T. |

GROUP III

| Patient Code No. | Latex Agglutination | I-Z Units | Clinical Diagnosis | Sex | Age | Response to anti-amebic drugs |
|---|---|---|---|---|---|---|
| 8 | + | 105 | Amebic liver abscesses hepatoma | M | 50 | + |
| 11 | − | 36 | Pneumonia | M | 20 | N.T. |
| Normal | − | 50 | — | M | — | N.T. |

GROUP IV

| Patient Code No. | Latex Agglutination | I-Z Units | Clinical Diagnosis | Sex | Age | Response to anti-amebic drugs |
|---|---|---|---|---|---|---|
| 9 | − | 86 | Hepatic amebiasis | M | 55 | + |
| 10 | − | 100 | Cirrhosis | M | 10 | N.T. |
| Normal | − | 50 | — | — | — | N.T. |

*N.T. = No treatment

GROUP V

| Patient Code No. | Latex Agglutination | I-Z Units | Clinical Diagnosis | Sex | Age | Response to anti-amebic drugs |
|---|---|---|---|---|---|---|
| 12 | − | 15 | Hepatitis | | 30 | N.T.* |
| 13 | − | 39 | Tuberculosis | | 44 | N.T. |
| Normal | − | 13 | — | — | — | N.T. |

GROUP VI

| Patient Code No. | Latex Agglutination | I-Z Units | Clinical Diagnosis | Sex | Age | Response to anti-amebic drugs |
|---|---|---|---|---|---|---|
| 14 | − | 19 | No definite diagnosis No amebiasis | F | − | N.T. |
| 15 | − | 100 | Hydatid cyst of lung | F | 16 | N.T. |
| 16 | − | 30 | Carcinoma of common bile duct | F | 25 | N.T. |
| 17 | − | 111 | Hepatoma | M | 70 | N.T. |
| 18 | − | 110 | Kala Azar | M | 18 | N.T. |
| Normal | − | 133 | − | − | − | N.T. |

GROUP VII

| Patient Code No. | Latex Agglutination | I-Z Units | Clinical Diagnosis | Sex | Age | Response to anti-amebic drugs |
|---|---|---|---|---|---|---|
| 19 | − | 72 | Carcinoma of stomach | M | 60 | N.T. |
| 20 | − | 80 | Pneumonia with effusion | M | 50 | N.T. |
| 21 | − | 85 | Typhoid fever | F | 20 | N.T. |
| 22 | − | 48 | Hydatid cyst of liver | F | 50 | N.T. |
| 23 | + | 200 | Amebic liver abscess | M | 38 | + |
| Normal | − | 34 | − | − | − | N.T. |

*N.T. - No treatment

GROUP VIII

| Patient Code No. | Latex Agglutination | I-Z Units | Clinical Diagnosis | Sex | Age | Response to anti-amebic drugs |
|---|---|---|---|---|---|---|
| 24 | − | 10 | Hydatid cyst of spleen | F | 37 | N.T.* |
| 25 | + | 70 | Amebic liver abscess | M | 45 | + |
| 26 | − | 30 | Hydatid cyst | F | 15 | N.T. |
| 27 | − | 32.5 | Amebic abscesses with superimposed infection | M | 45 | 1st responded to Flagyl, but fever disappeared with ampicillin** |
| 28 | − | 26 | Metastatic carcinoma of liver | M | 70 | N.T. |
| Normal | − | 22 | − | − | − | N.T. |

GROUP IX

| Patient Code No. | Latex Agglutination | I-Z Units | Clinical Diagnosis | Sex | Age | Response to anti-amebic drugs |
|---|---|---|---|---|---|---|
| 29 | − | 33.3 | Amebic liver abscesses | F | 35 | + |
| 30 | − | 11 | Pulmonary tuberculosis | F | 40 | N.T. |
| 31 | − | 25.3 | Metastatic adenocarcinoma | F | 40 | N.T. |
| Normal | − | 10 | − | − | − | N.T. |

*N.T. = No treatment
**WBC = 16,000 with 90 % polymorph. after ampicillin therapy fever disappeared.

GROUP X

| Patient Code No. | Latex Agglutination | I-Z Units | Clinical Diagnosis | Sex | Age | Response to anti-amebic drugs |
|---|---|---|---|---|---|---|
| 32 | − | 7.5 | Amebic liver abscesses | M | 20 | + |
| 33 | − | 11.6 | Amebic liver abscesses | M | 15 | + |
| 34 | − | 5 | Osteogenic sarcoma | M | 15 | N.T.* |
| 35 | − | 9 | Carcinoma of stomach and metastatic to liver | M | 45 | N.T. |
| 36 | − | 5 | Malignancy most likely Hodgkins | F | 32 | N.T. |
| Normal | − | 4.8 | − | − | − | N.T. |

*N.T. = No treatment

SUMMARY OF RESULTS

The best results were obtained in Groups I and II in which <1 I—Z units were developed in the controls and in blood samples from patients diagnosed as having ailments other than amebiasis and 17 to 19 I—Z units were developed in blood samples from patients (Nos. 2, 3 and 5) diagnosed as having some form of amebiasis and responding to anti-amebic drugs. For comparison, the latex agglutination test also showed positive results for these patients but also showed a false positive for one patient (No. 7) who did not have amebiasis based on clinical diagnosis.

Good results were also obtained in Groups III and VII in which the I—Z values from the blood of patients diagnosed as having amebiasis and responding to anti-amebic drugs (Nos. 8 and 23) were much higher than the values obtained from the controls and from the blood of patients diagnosed as having ailments other than amebiasis. The latex agglutination tests also correctly identified patients Nos. 8 and 23 as amebiasis patients while giving negative results for other (non-amebic) patients in these groups.

The Group VI tests were also satisfactory since all of the I-Z values for the non-amebic patients tested were lower than that of the control, which was consistent with the fact that none of the patients were diagnosed as having amebiasis. The latex agglutination tests on these patients were also negative.

In the Group VIII tests, the system of this invention clearly identified one case of amebiasis (No. 25) by an I—Z value much higher than those obtained from the control and from patients having other ailments. The other clinically diagnosed amebiasis case (No. 27) was only identified as a probable amebiasis case because its I—Z value was only slightly higher than those of patients with conditions other than amebiasis (Nos. 26 and 28). The latex agglutination test was positive for Patient No. 25 and negative for Patient No. 27, the latter being a false negative.

In the Group IV tests, the system of this invention identified the patient with amebiasis (No. 9) as a probable amebiasis case by an I-Z value substantially higher than that of the control, but lower than that of another patient (No. 10) who did not have amebiasis. (Conversely, the test of this invention could be considered as providing a false positive with respect to Patient No. 10). The latex agglutination test gave negative results for both Patients Nos. 9 and 10, the latter being a false negative.

In the Group V tests, the high I—Z value for Patient No. 13 in comparison with the control and with the value for the other patient in the Group would tend to indicate amebiasis where there was none. The latex agglutination tests were negative for both patients.

In the Group IX tests, the system of this invention identified the one patient who was clinically diagnosed as having amebiasis (No. 29) by the high I—Z value in comparison to the control. It would also tend to indicate amebiasis in another patient (No. 3) who did not have it because of an I-Z value almost as high as that of Patient No. 29. The latex agglutination tests for these patients were negative, being falsely negative for Patient No. 29.

In the Group X tests, the system of this invention identified one of the patients clinically diagnosed as having an amebiasis condition (No. 33) by an I-Z value substantially higher than that of the control. The other amebiasis patient (No. 32) was identified as a probable amebiasis case because the I—Z value, while high, was not as high as that of a patient (No. 35) who did not have amebiasis. (Conversely, the test of this invention could be considered as providing a false positive with respect to Patient No. 35). The latex agglutination tests were negative for all patients in this Group, being falsely negative with respect to Patients Nos. 32 and 33.

In the foregoing discussion of the results, it has been assumed that the clinical diagnosis is correct; and positive indications of an amebiasis condition in either the latex agglutination test or the test of this invention which are inconsistent with the clinical diagnosis have been termed "false positives". It is to be understood, however, that the designation "false positive" is not necessarily correct and that a positive indication of amebiasis in either the latex agglutination test or the test of this invention may indicate the presence of amebiasis at a subclinical level, the presence of intestinal amebiasis, or may indicate that the patient had had amebiasis in the past.

It is to be noted that in no case was there a false negative result obtained by the diagnostic system of this invention in contrast to the latex agglutination test which produced several false negatives. It is therefore apparent that the system of this invention is particularly applicable in screening procedures where false negatives are more detrimental than false positives.

In addition to the foregoing results on human patients with hepatic amebiasis, it has been found that the diagnostic system of this invention can reliably detect animals stimulated against amebic or gonococcal antigens. Naturally occurring pathological conditions in animals may also be detected and the use of the diagnostic system of this invention in veterinary medicine is also indicated.

The system of the present invention is advantageous over systems utilizing serum antibodies for detection of a pathological condition in that the present system utilizes cells capable of binding the antigen prior to the production of antibodies and is thereby capable of detecting a pathological condition at an earlier stage. In addition, the system of this invention is amenable to automation in contrast to serological which are difficult to automate.

The invention has been described with respect to specific embodiments. It will be understood, however, that modification and variations may be employed.

For example, as mentioned above, the washing of the blood cells treated with the antigen-enzyme detection agent complex for removal of unbound complex may be dispensed with and the unbound complex may be inactivated, rather than removed. One method for such inactivation is by heating (at 45° C. for 15 minutes) the mixture in the presence of fructose diphosphate.

Alternatively, the unbound complex can be removed by differential centrifugation of the mixture. particles In the above description, the control samples used were samples of blood from individuals free of the pathological condition for which the tests were run. However, if desired, a prepared control sample could be used containing particles of predetermined binding activity with respect to an antigen associated with the pathological condition. Such a material could be one in which antibodies to the antigen are absorbed onto beads of a gel of cross-linked dextran.

Other variations and modifications will be apparent to those skilled in the art.

What is claimed is:
1. A method for determining in a patient the presence or absence of a pathological condition which produces at least one specific immune response which comprises:
   a. extracting from the patient a sample of blood,
   b. providing a control sample containing particles of predetermined binding activity with respect to an antigen associated with said pathological condition,
   c. adding to at least the lymphocyte fraction of said patient's blood and of said control sample an excess of a detection agent comprising an antigen for said pathological condition linked to a marker material whereby a portion of said detection agent attaches to a portion of the lymphocytes in said lymphocyte fraction,
   d. eliminating from each of said lymphocyte fractions any unattached detection agent,
   e. determining the amount of attached detection agent in each of said lymphocyte fractions through determination of the amount of said marker material therein and calculating the amount of attached detection agent in each of said lymphocyte fractions per designated number of white blood cells, and
   f. comparing the amount of said marker material per designated number of white blood cells in said blood of said patient with the amount of said marker material per designated number of white blood cells in the blood of said control sample.

2. The method of claim 1 wherein said marker material is an enzyme.

3. The method of claim 2 wherein said enzyme is beta-galactosidase.

4. The method of claim 1 wherein said unattached detection agent is eliminated by the washing of said lymphocyte fraction.

5. The method of claim 1 wherein said pathological condition in an amebic infection and said antigen is derived from a culture of *Entamoeba histolytica*.

6. The method of claim 1 wherein said pathological condition is gonorrhea and said antigen is derived from a culture of *Neisseria gonorrheae*.

7. The method of claim 1 wherein said pathological condition is histoplasmosis and said antigen is derived from a culture of *Histoplasma capsulatum*.

8. The method of claim 1 wherein said pathological condition is a virus infection.

9. The method of claim 1 wherein said pathological condition is an allergic sensitivity.

10. The method of claim 1 wherein said control sample is a sample of blood from at least one individual free of said pathological condition.

11. A method for determining in a patient the presence or absence of a pathological condition which produces lymphocyte proliferation in the blood which comprises extracting from said patient a sample of blood, determining in said sample the proportion of lymphocytes containing receptors specific for an antigen for said pathological condition and comparing said proportion to the proportion of such lymphocytes in the blood of individual free of said pathological condition.

12. The method of claim 11 wherein the determination of said lymphocytes sensitive to an antigen for said pathological condition comprises attaching said lymphocytes to a detection agent comprising an antigen for said pathological condition linked to a marker material.

13. The method of claim 12 wherein said marker material is an enzyme.

14. The method of claim 13 wherein said enzyme is beta-galactosidase.

* * * * *